US00PP36203P2

(12) United States Plant Patent
Ward et al.

(10) Patent No.: US PP36,203 P2
(45) Date of Patent: Oct. 15, 2024

(54) ***PHILODENDRON* PLANT NAMED 'Princess Taffy'**

(50) Latin Name: *Philodendron erubescens*
Varietal Denomination: Princess Taffy

(71) Applicants: Matthew Ward, Worcester, MA (US); Kaila Ward, Worcester, MA (US)

(72) Inventors: Matthew Ward, Worcester, MA (US); Kaila Ward, Worcester, MA (US)

( * ) Notice: Subject to any disclaimer, the term of this patent is extended or adjusted under 35 U.S.C. 154(b) by 0 days.

(21) Appl. No.: 18/403,000

(22) Filed: Jan. 3, 2024

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./381
See application file for complete search history.

*Primary Examiner* — Susan McCormick Ewoldt
(74) *Attorney, Agent, or Firm* — James R. Holm; Plant Novelty Rights, LLC

(57) ABSTRACT

A new and distinct *Philodendron* plant named 'Princess Taffy' particularly distinguished by uniquely colored leaves having splotches and streaks of light yellow and brilliant yellow green, newly unfurled leaves prominently colored light yellow, and petioles streaked with purplish pink and yellowish green.

4 Drawing Sheets

Genus and species: *Philodendron erubescens.*
Cultivar denomination:
'Princess Taffy'.

BACKGROUND OF THE NEW PLANT

The present invention comprises a new and distinct cultivar of *Philodendron* plant, botanically known as *Philodendron erubescens*, and hereinafter referred to by the cultivar name 'Princess Taffy'.

This new *Philodendron* plant was discovered by the inventors as a spontaneous whole-plant mutation (sport) amongst a cultivated population of the unpatented *Philodendron* cultivar named 'White Princess'. The discovery of the new plant was made by the inventors in November 2022 in a non-publicly accessible area of a commercial greenhouse located in Worcester County, Massachusetts.

The new cultivar 'Princess Taffy' was selected due to its distinctive splotches and streaks of light yellow and brilliant yellow green on mature leaves. This color combination is not observed on leaves of the parent plant 'White Princess'. 'Princess Taffy' was first reproduced asexually using meristem tip cuttings in Worcester County, Massachusetts in June 2023. Asexual propagation by meristem tip cuttings of the new cultivar has shown that the unique features of the new cultivar are stable and reproduced true-to-type through three successive generations.

Plant Breeder's Rights for this cultivar have not been applied for. 'Princess Taffy' has not been made publicly available or sold anywhere in the world more than one-year prior to the effective filing date of this application.

SUMMARY OF THE INVENTION

The new *Philodendron* cultivar 'Princess Taffy' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Philodendron* cultivar. The combination of these characteristics distinguishes 'Princess Taffy' as a new and distinct cultivar of *Philodendron:*

1. Uniquely colored leaves having splotches and streaks of light yellow and brilliant yellow green; and
2. Petioles streaked with purplish pink and yellowish green.

DESCRIPTION OF THE PHOTOGRAPHS

This new *Philodendron* cultivar is illustrated by the accompanying-colored photographs which show the overall appearance and distinct characteristics of the plant. The colors shown are as true as can be reasonably obtained by conventional photographic procedures. The photographs are of 5-month-old plants grown in 4.5-inch round containers under moderate shade in a glass covered greenhouse in Worcester County, Massachusetts. Colors in the photographs may differ slightly from the color values cited in the botanical description which accurately describes the colors of the new cultivar.

Figure 1:
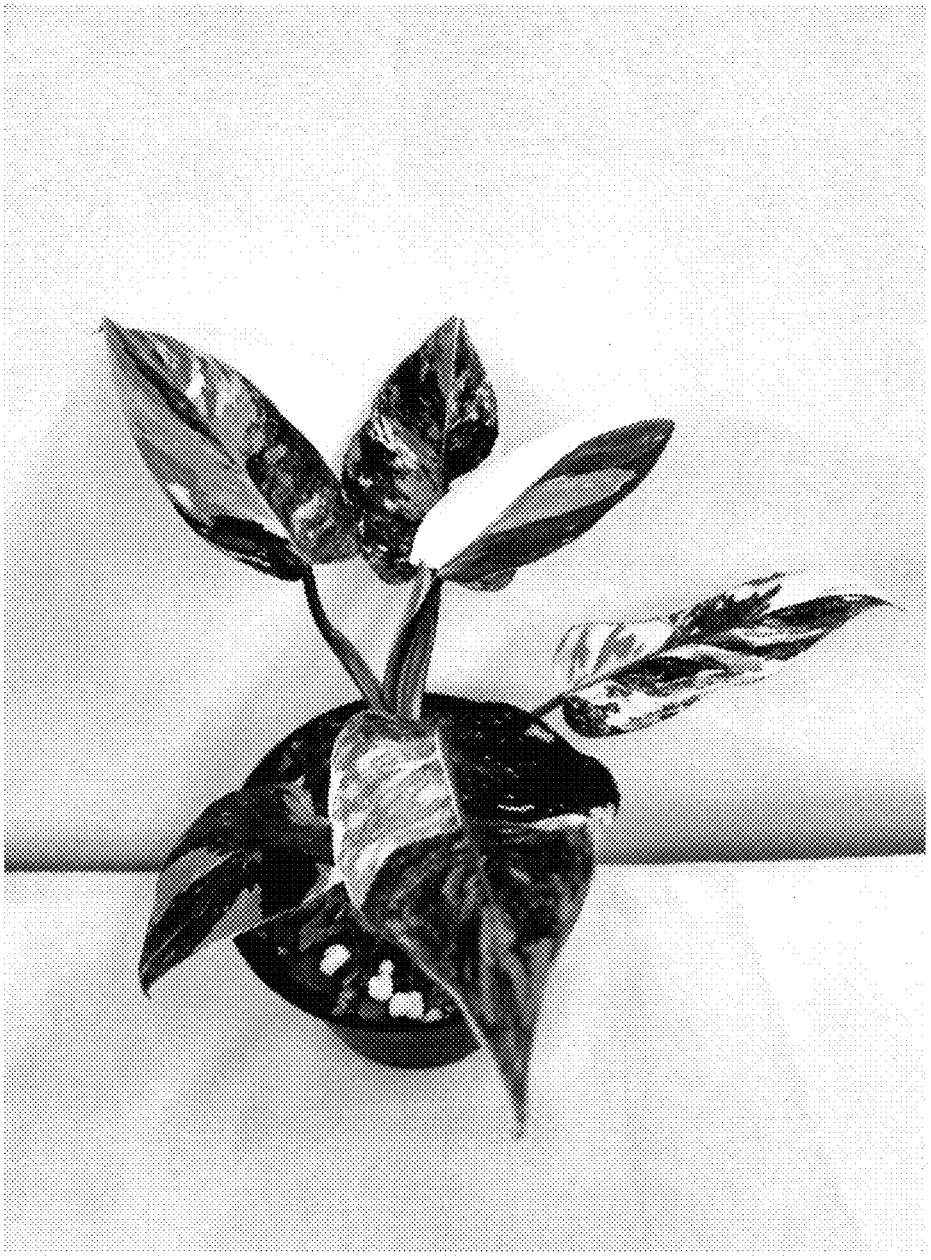

FIG. 1. shows the overall plant form and foliage of 'Princess Taffy'.

Figure 2:
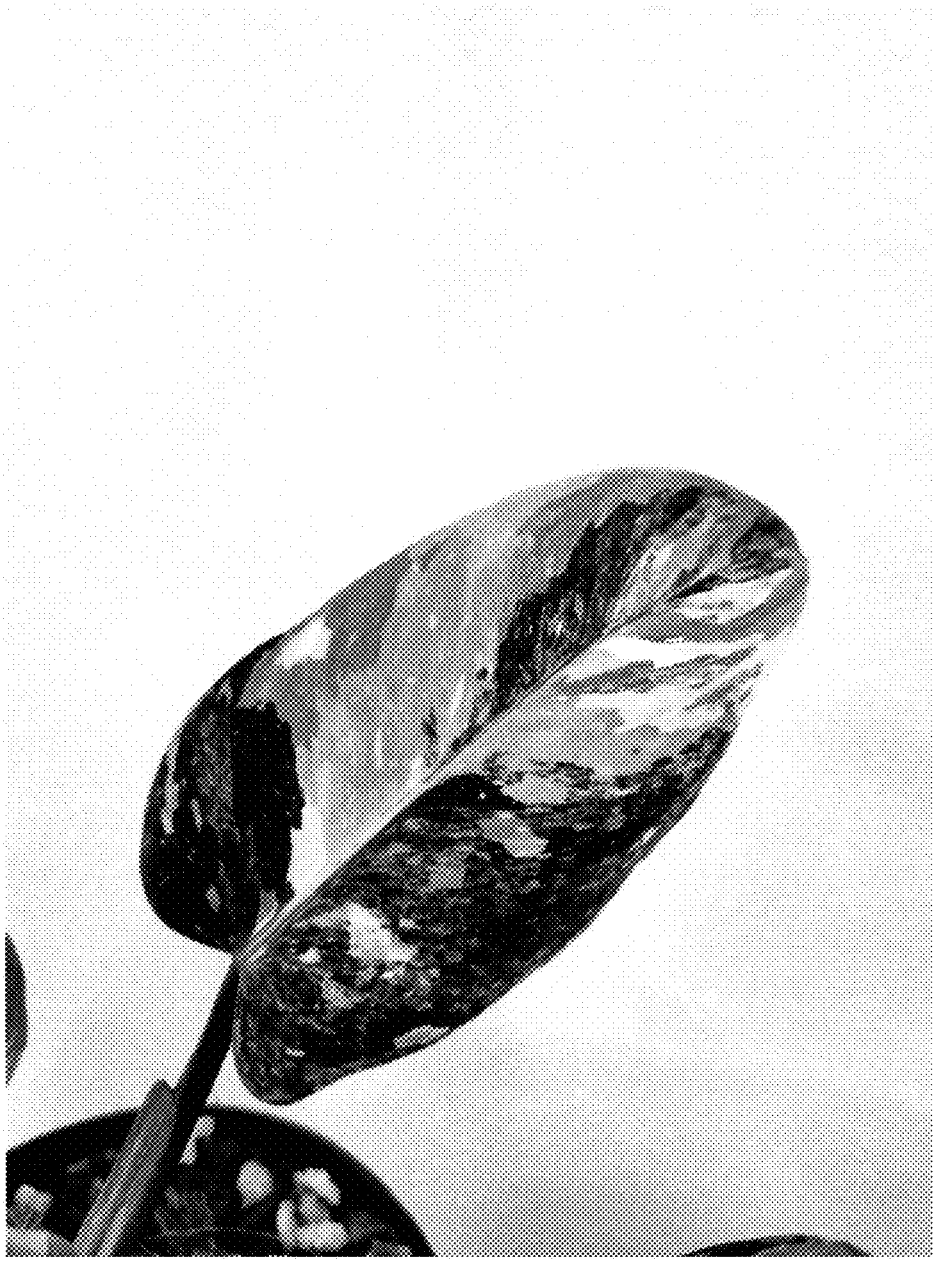

FIG. 2. shows a closeup of the upper surface of a mature leaf of 'Princess Taffy'.

Figure 3:
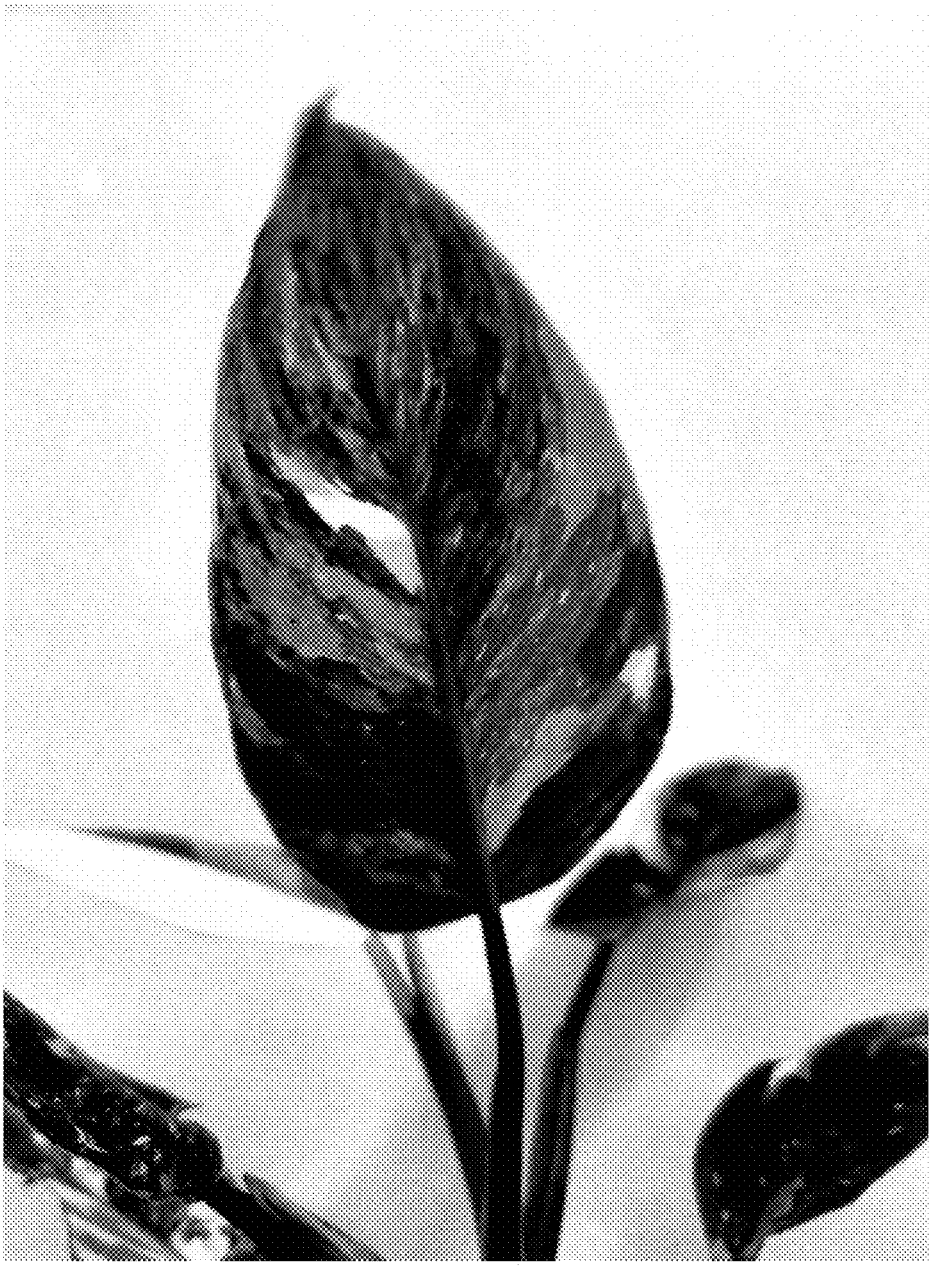

FIG. 3. shows a closeup of the lower surface of a mature leaf of 'Princess Taffy'.

Figure 4:
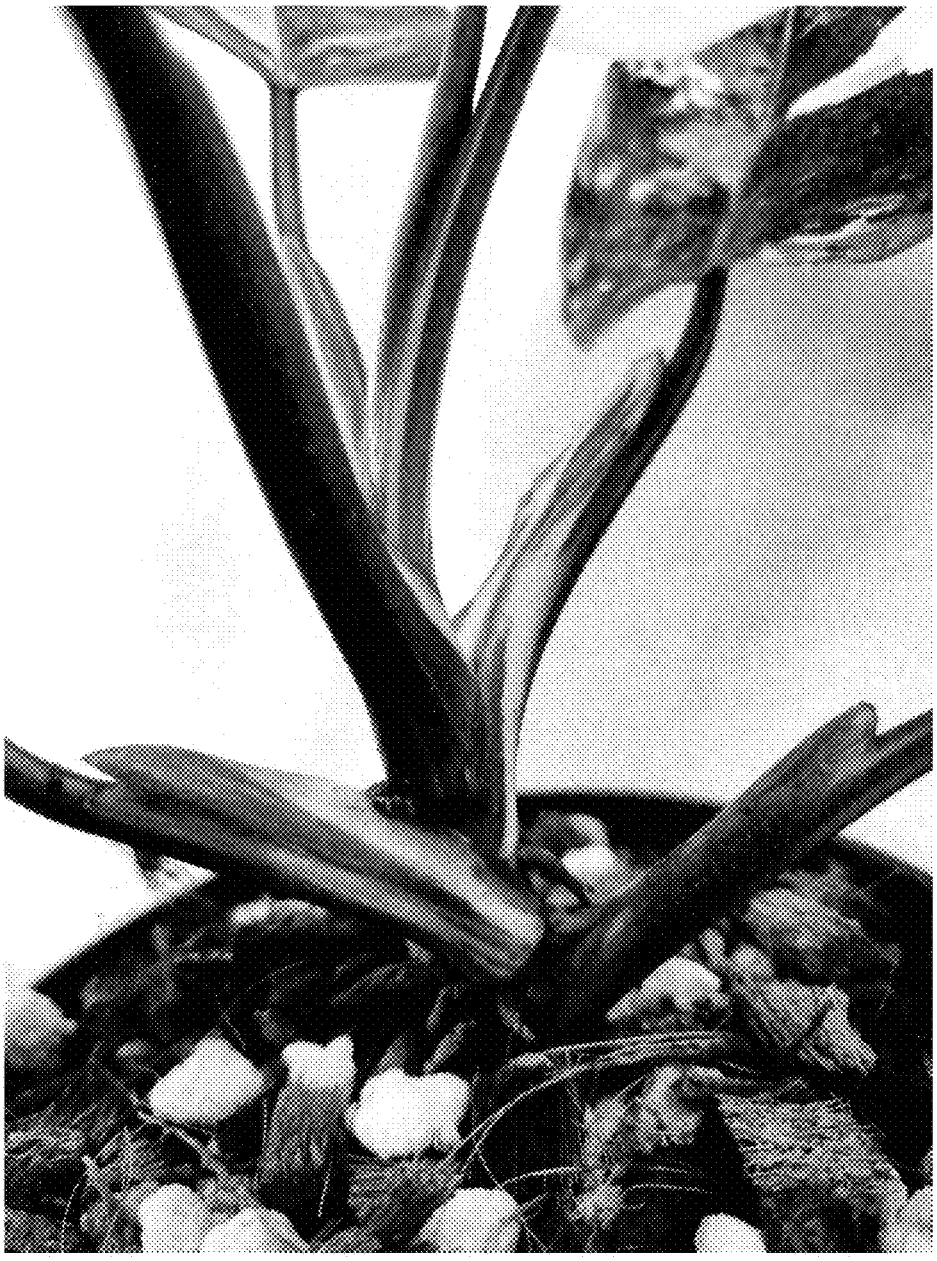

FIG. 4. shows a closeup of the main stem and inner crown of 'Princess Taffy'.

DESCRIPTION OF THE NEW CULTIVAR

In the following description, color references are made to The Royal Horticultural Society Colour Chart, Sixth Edition, except where general color terms of ordinary dictionary significance are used.

The following observations and measurements describe plants grown under moderate shade in a glass covered greenhouse in Worcester County, Massachusetts. Detailed descriptions were taken in November 2023 from 5-month-old plants grown in 4.5-inch round containers. Measurements and numerical values represent averages of typical plant types.

DETAILED BOTANICAL DESCRIPTION

Classification:

*Family*.—Araceae.

*Botanical*.—*Philodendron erubescens*.

*Common*.—Philodendron.

*Denomination*.—'Princess Taffy'.

General description:

*Plant type*.—Perennial tropical vine.

*Growth habit*.—Upright and vining.

*Height from soil level to top of foliar plane*.—Approximately 17.5 cm.

*Plant spread*.—Approximately 30.0 cm.

*Growth rate*.—Slow to Moderate.

*Branching characteristics*.—One main stem, weak basal branching.

*Main stem*.—Diameter: 1.0 cm. Length: 7.5 cm. Internode length: 1.3 cm. Texture and luster: Smooth, glabrous, and semi-glossy. Color: Deep yellowish green (141A) with streaks of yellowish white (196D). Number of leaves: 7.

*Propagation type*.—Meristem tip cuttings.

*Time to produce a rooted cutting*.—Approximately 2-3 weeks at an average of 70-80 degrees Fahrenheit.

Foliage description:

*Arrangement*.—Alternate.

*Attachment*.—Petiolate.

*Lamina*.—Shape: Between elliptic and ovate. Length (mature, fully expanded): 13.2 cm. Width (mature, fully expanded): 5.4 cm. Aspect: Moderately concave. Apex shape: Acuminate and slightly curved. Base shape: Truncate to slightly cordate. Texture and luster: Upper surface: Smooth, glabrous, and matte to slightly glossy. Lower surface: Smooth, glabrous, and glossy. Orientation: Newly unfurled leaves are held vertically; mature leaves are held horizontally to slightly upwards. Margins: Entire, moderately undulating. Color (mature foliage): Upper surface: Marbled, irregular splotches and streaks of moderate olive green (137A), greyed-white (156C), light yellow (10C to 10D), brilliant yellow green (150A) and greyish yellow green (191B). Lower surface: Marbled, irregular blotches and streaks of strong yellow green (144A to 144B), light greenish yellow (1C), greyed-white (156C), and pale green (189D). Color (immature, newly unfurled foliage): Upper surface: Marbled, predominantly colored light yellow (10C to 10D) with streaks of moderate olive green (137A), light greenish grey (191D), and yellowish white (NN155A to NN155B). Venation (mature leaf): Pattern: Arcuate. Color (upper surface): Indiscernible. Color (lower surface): Primary vein: Moderate yellowish pink (179C to 179D) from the base to the center of the lamina, coloration fades from the center towards the apex of the lamina. Secondary veins: Moderate olive green (137A).

*Petiole*.—Length: Approximately 5.0 cm. Diameter: At the base of the lamina, 0.5 cm. Wing: Shape: Rectangular, upwardly folded along the edges, and rounded at the tip. Length: Approximately 3.8 cm. Width: Approximately 1.0 cm. Color: Irregular streaks of light to pale purplish pink (62C and 62D), strong purplish pink (63C), deep purplish red (59B) and strong yellow green (143B); inner surface of the petiole wing is mostly light yellow green (144D) with slight streaking of light purplish pink (62C).

*Aerial roots*.—Three to four aerial roots present at each node, approximately 0.6 to 1.3 cm in length and colored yellow (11A) with tips colored deep purplish red (59B).

Inflorescence: None observed.

Cold tolerance: Not cold tolerant.

Disease and pest tolerance: None observed.

Fruit and seed set: None observed.

Drought tolerance: Moderate.

COMPARISON WITH PARENT VARIETY

'Princess Taffy' differs from the parent *Philodendron* plant named 'White Princess' (unpatented) in that 'Princess Taffy' has light yellow and brilliant yellow green colorations on the upper surface of mature leaves, whereas these light yellow and brilliant yellow green colorations are not present on any leaves of 'White Princess'. Additionally, leaves of 'Princess Taffy' have smaller areas of white and greyed-white colorations, whereas leaves of 'White Princess' have larger areas of white and greyed-white colorations.

COMPARISON WITH COMMERCIAL VARIETY

'Princess Taffy' differs from the commercial *Philodendron* plant named 'White Wizard' (unpatented) and the commercial *Philodendron* plant named 'White Night' (unpatented) in that 'Princess Taffy' has light yellow and brilliant yellow green colorations on the upper surface of mature leaves, whereas these light yellow and brilliant yellow green colorations are not present on any leaves of 'White Wizard' or 'White Night'. Additionally, the petioles of 'Princess Taffy' have streaks of purplish pink, purplish red, yellow and green, whereas the petioles of 'White Wizard' are colored solid green and the petioles of 'White Night' are colored dark purple.

We claim:

1. A new and distinct variety of *Philodendron* plant named 'Princess Taffy', substantially as illustrated and described herein.

* * * * *